United States Patent
Miyata et al.

(10) Patent No.: US 11,033,465 B2
(45) Date of Patent: Jun. 15, 2021

(54) DENTAL ADHESIVE COMPOSITION INCLUDING CHAIN TRANSFER AGENT

(71) Applicant: SHOFU INC., Kyoto (JP)

(72) Inventors: Shunsuke Miyata, Kyoto (JP); Hidefumi Fujimura, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

(21) Appl. No.: 16/357,377

(22) Filed: Mar. 19, 2019

(65) Prior Publication Data

US 2020/0016043 A1 Jan. 16, 2020

(30) Foreign Application Priority Data

Mar. 20, 2018 (JP) .............................. JP2018-052052
Mar. 15, 2019 (JP) .............................. JP2019-048084

(51) Int. Cl.
*A61K 6/30* (2020.01)
*A61K 6/71* (2020.01)
*A61K 6/62* (2020.01)

(52) U.S. Cl.
CPC .................. *A61K 6/30* (2020.01); *A61K 6/62* (2020.01); *A61K 6/71* (2020.01)

(58) Field of Classification Search
CPC ... A61K 6/30; A61K 6/71; A61K 6/62; A61K 6/16; A61K 6/887; A61K 6/884
See application file for complete search history.

(56) References Cited

U.S. PATENT DOCUMENTS

2004/0077746 A1  4/2004  Takeshita et al.

FOREIGN PATENT DOCUMENTS

| JP | 2009-539861 | 11/2009 |
| JP | 2014231493 A * | 12/2014 |
| JP | 2016-169180 | 9/2016 |
| JP | 2016-532640 | 10/2016 |
| WO | 2007/146210 | 12/2007 |
| WO | 2015/051217 | 4/2015 |

OTHER PUBLICATIONS

Shortall et al. "Refractive Index Mismatch and Monomer Reactivity Influence Composite Curing Depth", J. Dent. Res., 2008, vol. 87, No. 1, pp. 84-88.

* cited by examiner

*Primary Examiner* — Sanza L. McClendon
(74) *Attorney, Agent, or Firm* — Wenderoth, Lind & Ponack, L.L.P.

(57) ABSTRACT

To provide a one paste type dental adhesive composition which has mechanical characteristics and aesthetic property required in the restoration material, is superior in durable adhesive strength to the tooth substance, and is hard to be affected by the polymerization shrinkage stress and exhibits excellent durable adhesive strength even if the composition of the present invention is collectively filled and cured.
To provide a dental adhesive composition comprising: (a) an acidic group-non-containing polymerizable monomer, (b) an acidic group-containing polymerizable monomer, (c) a filler, (d) a photo polymerization initiator, and (e) a chain transfer agent, wherein the chain transfer agent (e) contains α-alkylstyrene compound.

20 Claims, No Drawings

DENTAL ADHESIVE COMPOSITION INCLUDING CHAIN TRANSFER AGENT

CROSS-REFERENCE TO RELATED APPLICATIONS

This application is based on and claims the benefit of priorities from Japanese Patent Application Serial No. 2018-052052 (filed on Mar. 20, 2018) and Japanese Patent Application Serial No. 2019-048084 (filed on Mar. 15, 2019), the contents of which are hereby incorporated by reference in their entirety.

BACKGROUND OF THE INVENTION

Field of the Invention

The present invention relates to a dental adhesive composition used in the dental field such as a dental adhesive material, a dental self-adhesive composite resin, a dental self-adhesive abutment building material, a dental resin cement, a dental self-adhesive surface coating material, a dental self-adhesive pit and fissure sealant, a dental self-adhesive manicure.

Description of the Related Art

In the dental clinical field, a dental filling composite resin has been used to esthetically and functionally restore a lost portion of a tooth caused by dental caries, tooth fracturing, etc. The dental filling composite resin is generally prepared by mixing a resin matrix including several types of polymerizable monomers, various filling materials such as an inorganic filler, an organic-inorganic composite filler, etc., and a polymerization initiator with each other into a uniform paste form.

Requirements demanded to a dental filling composite resin include high mechanical strength withstanding the occlusal pressure, a color tone and transparency similar to those of a natural tooth, a low polymerization shrinkage for preventing the generation of a contraction gap during the polymerization and the cure, a surface lubricating property during polishing and a gloss maintainability, high X-ray contrast property facilitating a prognosis diagnosis, sustained-release property of various ions such as fluorine to strengthen the tooth and to prevent secondary caries, and an excellent handling property for a dentist to execute a filling operation.

As the composite resin, a composite resin called bulk fill type and having high photo curing depth and reduced polymerization shrinkage has made an appearance. Since this has higher photo curing depth than the conventional composite resin and can be filled and cured collectively in a deep big cavity without stacking/filling, it is possible to shorten the time for a filling operation and a light irradiation to reduce a burden for the treatment of an operator and a patient. However, the volume polymerization shrinkage and the polymerization shrinkage stress applied to a cavity wall which occur during the polymerization remarkably increase by the collectively filling and curing in comparison with the case of the stacking/filling and curing, and therefore there remains a concern of a formation of a construction gap during the polymerization and a incidence of second caries caused thereby. Particularly, when the composite resin is cured by using a high-power light irradiation device which has been spread widely in recent, since a polymerization progressed rapidly, the polymerization shrinkage stress of the composite resin tends to increase in proportion to light irradiation strength.

In addition, a one paste type self-adhesive composite resin has made an appearance recently. This self-adhesive composite resin has adhesive property for an enamel and a dentin singly. Therefore, in the case of using this self-adhesive composite resin, because an adhesive operation by a bonding material which is required in the conventional composite resin is not required, restoration can be easily performed. In addition, in the case of using this self-adhesive composite resin, restoration can be easily performed by filling to a cavity and curing. Therefore, a technical error during adhesive restoration by operator, namely influence such as lack of the air drying during the adhesive operation by a bonding material and thickness control of an application layer of the bonding material can be removed. Accordingly, restoration which is more accurate and includes few errors can be expected.

However, it is necessary that a specific amount of an acid group-containing polymerizable monomer contained in a resin component for exhibiting tooth substance adhesive property of the self-adhesive composite resin is compounded in the composition in order to ensure sufficient adhesive strength. In other words, when a filling content of an inorganic filler is increased for improving a mechanical characteristic of the self-adhesive composite resin, adhesive property tended to decrease, and these were in a relation of the trade-off. Therefore, it is necessary to ensure a resin content of the specific amount for ensuring adhesive property and as a result, since the increase of the polymerization shrinkage due to polymerizing and curing of the resin components is invited, a problem of decreasing adhesive strength is caused by generating the polymerization shrinkage stress in the adhesive interface with the tooth substance to a pulling direction in which a tooth substance is peeled off. Therefore, the self-adhesive composite resin having stable durable adhesive property in a long period has been required in the present circumstances.

Furthermore, when the self-adhesive bulk fill type composite rein which is the one paste type self-adhesive composite resin having high photo curing depth is used, because the polymerization shrinkage stress is increased by the collectively photo-curing in addition to generating the polymerization shrinkage stress with the above specific amount of the resin content, it is very difficult to obtain stable durable adhesive property to a tooth substance in a long period.

Japanese Unexamined Patent Application Publication (Translation of PCT Application) No. 2009-539861 discloses a technique of containing photo-cleavable polymerizable monomers in order to reduce the polymerization shrinkage stress of the composite resin. This document further discloses these photo-cleavable polymerizable monomers can cleave a part of cross-linked network of a polymer formed by polymerization to reduce the volume polymerization shrinkage and polymerization shrinkage stress. However, there is a problem that when a content of the photo-cleavable polymerizable monomer increase too much, an increase of the viscosity and a decrease of the mechanical characteristic are caused.

Japanese Unexamined Patent Application Publication (Translation of PCT Application) No. 2016-532640 discloses a technique of adding polymerizeble stable radicals in order to reduce the polymerization shrinkage stress of the composite resin. This document further discloses that these radical chain transfer agents can delay a gelation point during the polymerization to reduce the polymerization shrinkage stress. However, by the result of investigation of the present inventors, it was confirmed that the reduction effect of the polymerization shrinkage stress by compounding the polymerizable stable radicals was poor and there is a tendency that photo curing depth is decreased remarkably when the content is increased.

Japanese Unexamined Patent Application Publication No. 2016-169180 discloses a technique of compounding an α-alkyl styrene compound into a high speed polymerization base photo polymerization initiator composition in which an α-diketone compound, an amine compound and a photo acid generator are combined. When the polymerizable composition containing the above described high speed polymerization base photo polymerization initiator is filled in the cavity, the polymerization shrinkage stress caused by the high speed polymerization reaction acts suddenly on an interface between the polymerization cured body and the cavity, and therefore a construction gap is easily generated. This documents further discloses that a polymerization cured body having both superior cavity wall compatibility and mechanical strength by compounding the α-alkyl styrene compound to the above described high speed polymerization base photo polymerization initiator because the polymerization shrinkage stress is suppressed. However, this document further discloses that this effect is exhibited by combining the high speed polymerization base composition and the α-alkyl styrene compound, and therefore sufficient mechanical strength and cavity wall compatibility are not obtained when the α-alkyl styrene compound is compounded to a general photo polymerization initiator base compound consisting of a conventional α-diketone compound and amine compound. In addition, the adhesive property for the tooth substance is not considered and the effect thereto is unknown.

As described above, there is no one paste type dental adhesive restoration material which has mechanical characteristics such as the hardness, the bending strength and the compressive strength and aesthetic property which are required in the filling restoration material, is hard to be affected by the polymerization shrinkage stress, and has excellent durable adhesive strength to the tooth substance.

Furthermore, when these restoration materials are filled and photo-cured collectively, the durable adhesive is not sufficient in clinical, therefore there remains a technical problem.

SUMMARY OF THE INVENTION

Technical Problem

An object of the present invention is to provide a dental adhesive composition used in the dental field such as a dental adhesive material, a dental self-adhesive composite resin, a dental self-adhesive abutment building material, a dental resin cement, a dental self-adhesive surface coating material, a dental self-adhesive pit and fissure sealant, a dental self-adhesive manicure which are used in the dental field, which is a dental adhesive restoration material having durable adhesive property capable of adhering to a biological hard tissue (an enamel and a dentin of a tooth) and the like in a long period, high mechanical characteristic capable of withstanding the occlusal pressure, and excellent color tone compatibility capable of using for an aesthetic restoration. Furthermore, the dental adhesive restoration material of the present invention has a feature that even if it is filled and cured collectively in a deep big cavity, it has good durable adhesive property capable of using without generating problems such as the clinical detachment.

Solution to Problem

The present inventors have made intensive studies, and as a result, have found it is possible to solve the above described problem by containing an α-alkyl styrene compound as a radical chain transfer agent in a photo curable restoration material having self-adhesive property, leading to completion of the present invention. In other words, it becomes possible to reduce the polymerization shrinkage stress while maintaining high curability by containing the α-alkyl styrene compound as the radical chain transfer agent. Therefore, it becomes possible to provide a self-adhesive restoration material without decreasing a mechanical characteristic and durable adhesive property to the tooth substance for the restoration material. Furthermore, it is possible to heighten transparency before curing to impart a deep photo curing depth capable of filling and curing collectively in a deep big cavity to the restoration material of the present invention by relatively approximating a refractive index of polymerizable component before curing and a refractive index of a filler. When the restoration material of the present invention is applied to the bulk fill type which is easily affected by such a polymerization shrinkage stress, the restoration material of the present invention exhibits the durable adhesive property to a tooth substance in a long period.

Although a mechanism that the dental adhesive composition of the present invention exhibits such superior effect is unknown, the following reasons are conjectured. Generally, the radical chain transfer agent has a character that the radical chain transfer agent receives a radical from a polymer chain which grew up by a radical polymerization once to stop the growth of the polymer, and thereafter, attacks the monomer again to form a radical of the monomer to start the polymerization again. In other words, a function to delay the formation of the polymer network during the polymerization (gelation point) is exhibited by stopping the polymer growth temporarily in this way. According to the character, when the content of the chain transfer agent increases, because the action of stopping the polymer growth becomes strong, there is a tendency to act as a polymerization prohibition agent to invite the decrease of the polymerization rate. However, it became clear that among radical chain transfer agents, the α-alkyl styrene compound has not only a superior delay effect of the gelation point but also a superior characteristic that it is hard to cause a decrease of the polymerization rate. In addition, there is a great advantage that the α-alkyl styrene compound maintains these characteristics after preserving at room temperature in a long period and has more superior preservation stability than other chain transfer agent. It is considered that the polymerization shrinkage stress is largely reduced to exhibit high mechanical characteristic and superior durable adhesive property by such a notable advantage of the α-alkyl styrene compound, in the dental adhesive composition of the present invention.

That is, the present inventors provide a dental adhesive composition comprising:

(a) an acidic group-non-containing polymerizable monomer, (b) an acidic group-containing polymerizable monomer, (c) a filler, (d) a photo polymerization initiator, and
(e) a chain transfer agent, wherein
the chain transfer agent (e) contains α-alkylstyrene compound.

Advantageous Effects of Invention

The present invention relates to a one paste type dental adhesive composition which has mechanical characteristics and aesthetic property which are required in the restoration material, and has excellent durable adhesive strength to the tooth substance. Furthermore, even if the composition of the present invention is collectively filled and cured, the composition is hard to be affected by the polymerization shrinkage stress, and exhibits excellent durable adhesive strength.

DETAILED DESCRIPTION OF THE PREFERRED EMBODIMENTS

Hereinafter, each components in the dental adhesive composition containing the chain transfer agent of the present invention is described in detail.

<(a) Acidic Group-Non-Containing Polymerizable Monomer>

The acidic group-non-containing polymerizable monomer (a) which can be used for the present invention can be any of known monofunctional and polyfunctional polymerizable monomers not having an acidic group commonly used in the dental field, without any limitation. Representative examples commonly suitably used include a (meth)acrylate polymerizable monomer or a (meth)acryloyl polymerizable monomer having an acryloyl group and/or a methacryloyl group. In the present invention, the term "(meth)acrylate" or "(meth)acryloyl" inclusively refers to both of an acryloyl group-containing polymerizable monomer and a methacryloyl group-containing polymerizable monomer.

Specific examples of a (meth)acrylate polymerizable monomer that can be used as the acidic group-non-containing polymerizable monomer (a) include the following.

Examples of a monofunctional monomer include (meth) acrylic acid esters such as methyl (meth)acrylate, ethyl (meth)acrylate, butyl (meth)acrylate (n-butyl (meth)acrylate, i-butyl (meth)acrylate), hexyl (meth)acrylate, dicyclopentenyl (meth)acrylate, tetrahydrofurfuryl (meth)acrylate, 2-hydroxyethyl (meth)acrylate, grycidyl (meth)acrylate, lauryl (meth)acrylate, cyclohexyl (meth)acrylate, benzil (meth)acrylate, allyl (meth)acrylate, 2-ethoxyethyl (meth) acrylate, methoxy polyethylene glycol (meth)acrylate, glycerol (meth)acrylate and isobornyl (meth)acrylate; silane compounds such as γ-(meth)acryloyloxy propyltrimethoxysilane and γ-(meth)acryloyloxy propyltriethoxysilane; nitrogen-containing compounds such as 2-(N,N-dimethylamino)ethyl (meth)acrylate, N-methylol (meth)acrylamide and diacetone (meth)acrylamide.

Examples of an aromatic difunctional monomer include 2,2-bis (4-(meth)acryloyloxy phenyl) propane, 2,2-bis (4-(3-(meth)acryloyloxy-2-hydroxypropoxy) phenyl) propane, 2,2-bis (4-(meth)acryloyloxy ethoxyphenyl) propane, 2,2-bis (4-(meth)acryloyloxy diethoxyphenyl) propane, 2,2-bis (4-(meth)acryloyloxy tetraethoxyphenyl) propane, 2,2-bis (4-(meth)acryloyloxy pentaethoxyphenyl) propane, 2,2-bis (4-(meth)acryloyloxy dipropooxyphenyl) propane, 2-(4-(meth)acryloyloxy ethoxyphenyl)-2-(4-(meth)acryloyloxy diethoxyphenyl) propane, 2-(4-(meth)acryloyloxy diethoxyphenyl)-2-(4-(meth)acryloyloxy triethoxyphenyl) propane, 2-(4-(meth)acryloyloxy dipropoxyphenyl)-2-(4-(meth)acryloyloxy triethoxyphenyl) propane, 2,2-bis (4-(meth)acryloyloxy dipropoxyphenyl) propane and 2,2-bis(4-(meth)acryloyloxy isopropoxyphenyl) propane.

Examples of an aliphatic difunctional monomer include 2-hydroxy-3-acryloyloxypropyl methacrylate, hydroxypivalic acid neopentylglycol di(meth)acrylate, ethyleneglycol di(meth)acrylate, diethyleneglycol di(meth)acrylate, triethyleneglycol di(meth)acrylate, butyleneglycol di(meth)acrylate, neopentylglycol di(meth)acrylate, propyleneglycol di(meth)acrylate, polyethyleneglycol di(meth)acrylate, 1,3-butanediol di(meth)acrylate, 1,4-butanediol di(meth)acrylate, 1,6-hexanediol di(meth)acrylate, and glycerin di(meth) acrylate.

Examples of a trifunctional monomer include trimethylolpropane tri(meth)acrylate, trimethylolethane tri(meth)acrylate, trimethylolmethanet tri(meth)acrylate, pentaerythritol tri(meth)acrylate, etc.

Examples of a tetrafunctional monomer include pentaerythritol tetra(meth)acrylate and ditrimethylolporpane tetra(meth)acrylate.

Examples of a urethane polymerizable monomer include di(meth)acrylates having a bifunctionality, trifunctionality or more-functionality and urethane linkage, which are derived from an adduct of a polymerizable monomer having a hydroxy group such as 2-hydroxyethyl (meth)acrylate, 2-hydroxypropyl (meth)acrylate and 3-chloro-2-hydroxypropyl (meth)acrylate, and a diisocyanate compound such methylcyclohexane diisocyanate, methylene bis(4-cyclohexyl isocyanate), hexamethylene diisocyanate, trimethyl hexamethylene diisocyanate, isophorone diisocyanate, diisocyanate methylbenzene and 4,4-diphenylmethane diisocyanate.

An oligomer or a prepolymer having at least one polymerizable group in its molecule may be used other than such a (meth)acrylate polymerizable monomer, without any limitation. There is no problem even if a substituent such as a fluoro group is contained in the same molecule.

The polymerizable monomers described above can be used not only singly but also in combinations of a plurality thereof.

<(b) Acidic Group-Containing Polymerizable Monomer>

The acidic group-containing polymerizable monomer (b) contained in the dental adhesive composition of the present invention exhibits adhesive property by interacting with a biological hard tissue (an enamel and a dentin of a tooth) or the like which is to be an adherend.

As the acidic group-containing polymerizable monomer (b) which can be used for the dental adhesive composition of the present invention, any polymerizable monomer as long as the polymerizable monomer contains acidic group can be used without any limitation. Specific examples of the acidic group of the acidic group-containing polymerizable monomer (b) are not limited to, but include a phosphoryl group, a pyrophosphoryl group, a phosphonyl group, a carboxylic acid group, a sulfonyl group, and a thiophosphoryl group. In addition, any acidic group-containing polymerizable monomers may be used without any limitation regardless of the number or the type of radical polymerizable unsaturated groups (monofunctional group or multifunctional groups) of the acidic group-containing polymerizable monomer (b). Specific examples of the unsaturated group of the acidic group-containing polymerizable monomer (b) are not limited to, but include an acryloyl group, a methacryloyl group, a styryl group, a vinyl group, and an aryl group. It is preferable that an acidic group-containing polymerizable monomer has an acryloyl group and/or a methacryloyl group among these unsaturated groups.

Further, these acidic group-containing polymerizable monomers (b) may contain together other functional group such as an alkyl group, halogen, an amino group, a glycidyl group, and a hydroxy group in a molecule. In addition, not only a monomer with a short main chain but also be an oligomer, a prepolymer, or the like with a long main chain may be used as the acidic group-containing polymerizable monomer (b) without any limitation. Further, derivatives of the acidic group-containing polymerizable monomer (b) such as a metallic salt, an ammonium salt, and an acid chloride obtained by partially neutralizing the acidic group of the acidic group-containing polymerizable monomer (b) may also be used to the extent that the adhesive property to various adherends is not adversely affected.

Specific examples of an acidic group-containing polymerizable monomer that can be used as the acidic group-containing polymerizable monomer (b) include the following. In the present specification, the term "(meth)acrylate" or "(meth)acryloyl" inclusively refers to both of an acryloyl group-containing polymerizable monomer and a methacryloyl group-containing polymerizable monomer.

Specific examples of an acidic group-containing polymerizable monomer which has a phosphoryl group are not limited to, but include (meth)acryloyloxymethyl dihydrogen phosphate, 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, di(meth) acryloyloxyethyl hydrogensphosphate, di(meth) acryloyloxybutyl hydrogen phosphate, di(meta) acryloyloxyhexyl hydrogen phosphate, di(meth) acryloyloxyoctyl hydrogen phosphate, di(meth) acryloyloxynonyl hydrogen phosphate, di(meth) acryloyloxydecyl hydrogen phosphate, 1,3-di (meth) acryloyloxypropyl-2-dihydrogenphosphate, 2-(meth) acryloyloxyethylphenyl hydrogen phosphate, 2-(meth) acryloyloxyethyl 2'-bromoethyl hydrogen phosphate and (meth) acryloyloxyethylphenyl phosphonate.

Specific examples of an acidic group-containing polymerizable monomer which has a pyrophosphoryl group are not limited to, but include, di [2-(meth) acryloyloxyethyl] pyrophosphate, di [3-(meth) acryloyloxypropyl] pyrophosphate, di [4-(meth) acryloyloxybutyl] pyrophosphate, di [5-(meth) acryloyloxypentyl] pyrophosphate, di [6-(meth) acryloyloxyhexyl] pyrophosphate, di [7-(meth) acryloyloxyheptyl] pyrophosphate, di [8-(meth) acryloyloxyoctyl] pyrophosphate, di [9-(meth) acryloyloxynonyl] pyrophosphate, di [10-(meth) acryloyloxydecyl] pyrophosphate, di [12-(meth) acryloyloxydodecyl] pyrophosphate, tetra [2-(meth) acryloyloxyethyl] pyrophosphate, tri [2-(meth) acryloyloxyethyl] pyrophosphate.

Specific examples of a polymerizable monomer which has a carboxylic acid group are not limited to, but include (meth) acrylic acid, 2-chloro (meth) acrylic acid, 3-chloro (meth) acrylic acid, 2-cyano (meth) acrylic acid, aconitic acid, mesaconic acid, maleic acid, maleic anhydride, itaconic acid, itaconic anhydride, fumaric acid, glutaconic acid, citraconic acid, utraconic acid, 1,4-di(meth) acryloyloxyethylpyromellitic acid, 6-(meth) acryloyloxynaphthalene-1,2,6-tricarboxylic acid, 1-buten1,2,4-tricarboxylic acid, 3-buten1,2,3-tricarboxylic acid, N-(meth) acryloyl-p-aminobenzoic acid, N-(meth) acryloyl-5-aminosalicylic acid, 4-(meth) acryloyloxyethyltrimellitic acid and anhydride thereof, 4-(meth) acryloyloxybutyltrimellitic acid and anhydride thereof, 2-(meth) acryloyloxybenzoic acid, 6-(meth) acryloyloxyethyl hydrogen succinate, 6-(meth) acryloyloxyethyl hydrogen maleate, 11-(meth) acryloyloxy-1,1-undecanedicarboxylic acid, p-vinylbenzoic acid, 4-(meth) acryloyloxyethoxycarbonylphthalic acid, 4-(meth) acryloyloxybutyloxycarbonylphthalic acid, 4-(meth) acryloyloxyhexyloxycarbonylphthalic acid, 4-(meth) acryloyloxyoctyloxycarbonylphthalic acid, 4-(meth) acryloyloxydecyloxycarbonylphthalic acid and anhydride thereof, 5-(meth) acryloylaminopentylcarboxylic acid, 6-(meth) acryloyloxy-1,1-hexanedicarboxylic acid, 8-(meth) acryloyloxy-1,1-octanedicarboxylic acid, 10-(meth) acryloyloxy-1, 1-decanedicarboxylic acid, and 11-(meth) acryloyloxy-1,1-undecanedicarboxylic acid.

Specific examples of an acidic group-containing polymerizable monomer which has a phosphonyl group are not limited to, but include acidic group-containing polymerizable monomeres such as 5-(meth)acryloyloxy pentyl-3-phosphonopropionate, 6-(meth)acryloyloxy hexyl-3-phosphonopropionate, 10-(meth)acryloyloxy decyl-3-phosphonopropionate, (6-methacryloxy) hexylphosphonoacetate, 6-(meth)acryloyloxy hexyl-3-phosphonoacetate, and 10-(meth)acryloyloxy decyl-3-phosphonoacetate.

Specific examples of an acidic group-containing polymerizable monomer which has a sulfonate group are not limited to, but include acidic group-containing polymerizable monomers such as 2-(meth)acrylamido-2-methylpropane sulfonic acid, styrene sulfonic acid, 2-sulfoethyl (meth) acrylate, 4-(meth)acryloyloxy benzenesulfonic acid, and 3-(meth)acryloyloxy propanesulfonic acid.

These acid group-containing polymerizable monomers can be used alone, or in a combination thereof.

Among these acid group-containing polymerizable monomers, it is preferable to use 10-methacryloyloxydecyl dihydrogenphosphate, (6-methacryloxy) hexyl phosphonoacetate, 6-methacryloyloxy hexyl-3-phosphonoacetate, 4-methacryloyloxyethyl trimellitate and anhydride thereof, 4-acryloyloxyethyl trimellitate and anhydride thereof or the like.

It is preferable that the dental adhesive composition of the present invention contains the acidic group-non-containing polymerizable monomer (a) and the acidic group-containing polymerizable monomer (b) in a weight ratio of the acidic group-non-containing polymerizable monomer (a): the acid group-containing polymerizable monomer (b)=99:1 to 70:30, more preferably 95:5 to 80:20. When the weight ratio of the acidic group-containing polymerizable monomer (b) is less than 1, the effect of the self-adhesive property to a biological hard tissue (such as an enamel and a dentin of the natural tooth) is not observed. On the other hand, when the weight ratio of the acidic group-containing polymerizable monomer (b) is more than 30, polymerization of other polymerizable monomers may be hindered to cause a problem such as a decrease of mechanical strength.

<(f) Acidic Group-Non-Containing Hydrophilic Polymerizable Monomer>

In addition, in order to provide the dental adhesive composition of the present invention with high self-adhesive property to the tooth substance, it is preferable that the dental adhesive composition of the present invention contains an acidic group-non-containing hydrophilic polymerizable monomer (f) as a part of the acidic group-noncontaining polymerizable monomer (a). When the dental adhesive composition contains the acidic group-non-containing hydrophilic polymerizable monomer (f), the wettability of the dental adhesive composition with a biological hard tissue (such as an enamel and a dentin of the natural tooth) to be an adherend can be improved to increase adhesive property.

Herein, polymerizable monomers that resolve in an amount of 10 parts by weight or more in 100 parts by weight of water at 23° C. is defined as hydrophilic polymerizable monomers, and other polymerizable monomers are defined as hydrophobic polymerizable monomers. That is, 10 g of a polymerizable monomer is added to 100 g of water kept at 23° C. in a sample bottle, and the mixture is stirred for 10 minutes to thereafter be left to stand. After the lapse of 10 minutes, the mixture in the sample bottle is observed. If the mixture is resolved uniformly transparently or translucently, the polymerizable monomer is determined as a hydrophilic polymerizable monomer. If not, the polymerizable monomer is determined as a hydrophobic polymerizable monomer.

Specific examples of the acidic group-non-containing hydrophilic polymerizable monomer (f) which can be used for a dental adhesive composition of the present invention include 2-hydroxyethyl (meth)acrylate, 2-hydroxypropyl (meth)acrylate, 3-hydroxypropyl (meth)acrylate, 1,2-dihydroxypropyl (meth)acrylate, 1,3-dihydroxypropyl (meth)acrylate, 2,3-dihydroxypropyl (meth)acrylate, 2-hydroxypropyl-1,3-di(meth)acrylate, 3-hydroxypropyl-1,2-di(meth)acrylate, pentaerythritol di(meth)acrylate, 2-trimethylammoniumethyl (meth)acrylchloride, (meth)acrylamide, 2-hydroxyethyl (meth)acrylamide, polyethylene glycol di(meth)acrylate (the number of oxyethylene groups is greater than or equal to 9), 2-hydroxy-3-acryloiloxy propylmethacrylate, 2-hydroxy-1-3-dimethacryloyloxy propane, dimethylacrylamide, acryloylmorpholine, isopropyl acrylamide, diethylacrylic amide, dimethylamino propylacryl amide and hydroxyethylacrylamide, though the acidic group-non-containing hydrophilic polymerizable monomer is not limited to such.

Such acidic group-non-containing hydrophilic polymerizable monomers (f) may be used singly or in various combinations. Among these acidic group-non-containing hydrophilic polymerizable monomers (f), those which resolve in an amount of 20 parts by weight or more in 100 parts by weight of water at 23° C. are preferable, and those which resolve in an amount of 40 parts by weight or more in 100 parts by weight of water at 23° C. are more preferable. Specific examples of that include 2-hydroxyethyl (meth)acrylate, polyethyleneglycol di(meth)acrylate (in which the number of oxyethylene groups is 9), polyethyleneglycol di(meth)acrylate (in which the number of oxyethylene groups is 14), polyethyleneglycol di(meth)acrylate (in which the number of oxyethylene groups is 23), 2-hydroxy-3-acryloiloxy propylmethacrylate, 2-hydroxy-1-3-dimethacryloyloxy propane, dimethylacrylamide, acryloylmorpholine, isopropyl acrylamide, diethylacrylic amide, dimethylamino propylacryl amide, hydroxyethylacrylamide or the like.

A content of the acidic group-non-containing hydrophilic polymerizable monomer (f) which can be used for the dental adhesive composition of the present invention is preferably 5 to 70 parts by weight in 100 parts by weight of the acidic group-non-containing polymerizable monomer (a), and more preferably 7 to 60 parts by weight, further preferably 10 to 50 parts by weight. When the content of the acidic group-non-containing hydrophilic polymerizable monomer (f) in the acidic group-non-containing polymerizable monomer (a) is more than 70 parts by weight, polymerization of other polymerizable monomers may be hindered to adversely affect the physical properties. When the content of the acidic group-non-containing hydrophilic polymerizable monomer (f) is less than 5 parts by weight, on the other hand, the wettability with a biological hard tissue may be poor.

In order to provide the dental adhesive composition of the present invention with adhesive property to precious metal, it is also effective for the purpose of the present invention to use a polymerizable monomer containing a sulfur atom in a molecule. Any polymerizable monomer containing a sulfer atom in a molecule may be used irrespective of the type and the number of unsaturated groups, the presence or absence of other functional groups, and so forth.

Specific examples of polymerizable monomers having a sulfur atom which can be used for the dental adhesive composition of the present invention include, but are not limited to, (meth)acrylate having a triazinethiol group, (meth)acrylate having a mercapto group, (meth)acrylate having a polysulfide group, (meth)acrylate having a thiophosphate group, (meth)acrylate having a cyclic disufide group, (meth)acrylate having a mercaptodithiazole group, (meth)acrylate having a thiouracil group, (meth)acrylate having a thiirane group, or the like. Such polymerizable monomers containing a sulfur atom in a molecule may be used singly or in various combinations.

In order to provide the dental adhesive composition of the present invention with adhesive property to ceramics, composite resins, and so forth, it is also effective for the purpose of the present invention to use an organosilane compound having at least one polymerizable unsaturated group in a molecule. Any organosilane compound having a polymerizable unsaturated group in a molecule may be used irrespective of the type and the number of unsaturated groups, the presence or absence of other functional groups, and so forth. Such organosilane compounds may be used singly or in various combinations.

Specific examples of organosilane compounds having a polymerizable unsaturated group which can be used for the dental adhesive composition of the present invention include, but are not limited to, vinyltrimethoxysilane, vinyltriethoxysilane, vinyltrichlorosilane, vinyl(β-methoxyethoxy)silane, γ-methacryloxypropyl trimethoxysilane, γ-glycidoxypropyl trimethoxysilane, γ-mercaptopropyl trimethoxysilane or the like.

<(c) Filler>

As the filler (c) that can be used for the present invention, a known filler commonly used in a dental composite material can be used. The filler (c) includes an inorganic filler, an organic filler and an organic/inorganic composite filler, and these fillers can be used not only singly but also in combinations of a plurality thereof regardless of the types of the fillers.

Specific examples of the inorganic filler include silica, aluminum silicate, alumina, titania, zirconia, various glasses (including fluoride glass, borosilicate glass, soda glass, barium glass, barium aluminum silica glass, glass including strontium or zirconium, glass ceramics, fluoroaluminosilicate glass, and synthetic glass by a sol-gel method), Aerosil (registered trademark), calcium fluoride, strontium fluoride, calcium carbonate, kaolin, clay, mica, aluminum sulfate, calcium sulfate, barium sulfate, titanium oxide, calcium phosphate, hydroxyapatite, calcium hydroxide, strontium hydroxide and zeolite. Such an inorganic filler may also be used as an aggregate, and examples of the aggregate include a silica-zirconia composite oxide aggregate obtained by mixing silica sol and zirconia sol and subjecting the mixture to spray drying and a heat treatment.

Examples of the organic filler include elastomers such as polyvinyl acetate, polyvinyl alcohol and a styrene-butadiene rubber, non-crosslinkable (meth)acrylate polymers each being a homopolymer of a monofunctional (meth)acrylate polymerizable monomer, such as polymethyl methacrylate (PMMA), polyethyl methacrylate, polypropyl methacrylate and polybutyl methacrylate, crosslinkable (meth)acrylate polymers obtained by copolymerizing a monofunctional (meth)acrylate polymerizable monomer with a polymerizable monomer having two or more functional groups, and polyvinyl acetate, polyethylene glycol, polypropylene glycol and polyvinyl alcohol, but are not limited thereto.

In addition, examples of the organic/inorganic composite filler include one obtained by covering the surface of a filler with a polymerizable monomer by polymerization, one obtained by mixing a filler and a polymerization monomer and polymerizing the monomer, and thereafter grinding the resultant to a proper particle size, or one obtained by dispersing a filler in a polymerizable monomer in advance for emulsion polymerization or suspension polymerization, but are not limited thereto at all.

As such a filler, a filler having any shape such as a spherical shape, a needle shape, a plate shape, a crushed shape or a scale shape can be used. The average particle diameter of the filler is different depending on the type of the filler, and in the case of the inorganic filler, any filler can be used as long as it has an average particle diameter within a range of 0.01 to 20 μm, preferably within a range of 0.01 to 10 μm, more preferably within a range of 1 to 5 μm. In the case of the organic/inorganic composite type filler, any filler can be used as long as it has an average particle diameter within a range of 0.05 to 100 μm, preferably within a range of 0.5 to 50 μm, more preferably within a range of 1 to 30 μm. Furthermore, in the case of the organic filler, the average particle diameter is not particularly limited, and any filler having an average particle diameter in any range can be used. Herein, the information on the average particle diameter can be examined by a laser diffraction type particle size measurement machine. When the filler (c) is an aggregate, the above average particle diameter corresponds to the average particle diameter of the aggregate. The average particle diameter of the filler is preferably within a range of 0.1 to 20 μm, more preferably within a range of 0.1 to 10 μm. Herein, the information on the average particle diameter and the variation coefficient of the particle size, and the like can be examined by a laser diffraction type particle size measurement machine, and when the filler (c) is an aggregate, the above average particle diameter corresponds to the average particle diameter of the aggregate. When the average particle diameter is less than 0.1 μm, the dental adhesive composition is sticky and gas bubbles are easily incorporated. When the average particle diameter is more than 20 μm, the surface lubricity of the dental adhesive composition after polishing may be decreased.

The surface of the filler may also be multi-functionalized by a surface treatment method using a surface treatment agent, and the filler subjected to a surface treatment can be used without any limitation. Specific examples of the surface treatment agent for use in multi-functionalizing the surface of the filler include a surfactant, a fatty acid, an organic acid, an inorganic acid, various coupling materials (a titanate coupling agent, an aluminate coupling agent and a silane coupling agent), and a metal alkoxide compound. Specific examples of the surface treatment method include a method of spraying the surface treatment agent from above in the state of allowing the filler to flow, a method of dispersing the filler in a solution including the surface treatment agent, and a method of applying several surface treatment agents on the surface of the filler by a multilayer treatment. The surface treatment agent and the surface treatment method, however, are not limited thereto. Moreover, each of the surface treatment agent and the surface treatment method can be used singly or in combination compositely.

Examples of the silane coupling agent include γ-methacryloxypropyl trimethoxysilane and γ-methacryloxypropyl triethoxysilane. Preferably, γ-methacryloxypropyl trimethoxysilane is used. The aggregate and the filler may be subjected to a surface treatment with the same coupling agent or a different coupling agent.

A content of the filler (c) which can be used for the dental adhesive composition of the present invention is not particularly limited, but is preferably 50 to 900 parts by weight based on 100 parts by weight of a total content of a resin component consisting of the acidic group-non-containing polymerizable monomer (a), the acidic group-containing polymerizable monomer (b), the photo polymerization initiator (d) and the chain transfer agent (e) which are contained in the dental adhesive composition, more preferably 70 to 800 parts by weight. When the content of the filler (c) is less than 50 parts by weight, it may be not possible to obtain sufficient mechanical strength. In addition, because the content of the acidic group-non-containing polymerizable monomer (a) and the content of the acidic group-containing polymerizable monomer (b) increase, the polymerization shrinkage increases. Therefore, a possibility to cause a problem that a construction gap is formed between the restoration and the cavity wall becomes large. In addition, when the content of the filler (c) is more than 900 parts by weight, it may be difficult to obtain a dental adhesive composition in which fillers are dispersed uniformly. Further, a possibility to decrease the self-adhesive property to the tooth substance may become high because the content of the acidic group-containing polymerizable monomer (b) relatively decreases with the increase of the content of the filler.

<(d) Photo Polymerization Initiator>

The photo polymerization initiator (d) which is used for the dental adhesive composition of the present invention is not particularly limited, and any known photo polymerization initiator commonly used in the dental field may be used without any limitation.

For the photo polymerization initiator, photosensitizers, and photosensitizers/photopolymerization promotors or the like may be suitably used. Specific examples of the photosensitizers include α-diketones such as benzil, camphorquinone, α-naphtil, acetonaphtone, p,p'-dimethoxybenzil, p,p'-dichlorobenzylacetyl, pentadione, 1,2-phenanthrenquinone, 1,4-phenanthrenquinone, 3,4-phenanthrenquinone, 9,10-phenanthrenquinone and naphthoquinone; benzoin alkyl ethers such as benzoin, benzoin methyl ether and benzoin ethyl ether; thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone and 2,4-diisopropylthioxanthone; benzophenones such as benzophenone, p-chlorobenzophenone and p-methoxybenzophenone; acylphosphineoxides such as 2,4,6-trimethylbenzoyl diphenylphosphineoxide and bis(2,6-dimethoxybenzoyl)-2,4,4-trimethylpentylphosphineoxide; α-aminoacetophenones such as 2-benzyl-dimethylamino-1-(4-morpholinophenyl)-butanone-1,2-benzyl-diethylamino-1-(4-morpholinophenyl)propanone-1; ketals such as benzyldimethylketal, benzyldiethylketal and benzyl(2-methoxyethylketal); titanocenes such as bis(cyclopentadienyl)-bis[2,6-difluoro-3-(1-pyrolyl)phenyl]titanium, bis(cyclopentadienyl)-bis(pentanefluorophenyl)titanium and bis(cyclopentadienyl)-bis(2,3,5,6-tetrafluoro-4-disiloxyphenyl)-titanium.

Specific examples of the photopolymerization promotor include tetriary amines such as N,N-dimethylaniline, N,N-diethylaniline, N,N-di-n-butylaniline, N,N-dibenzylaniline, p-N,N-dimethyl-toluidine, m-N,N-dimethyl-toluidine, p-N,N-diethyl-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoicacid ethyl ester, p-dimtethylaminobenzoic acid amino ester, N,N-dimethylanthranilic acid methyl ester, N,N-dihydroxyethylaniline, p-N,N-dihydroxyethyl-toluidine, p-dimethylaminophenylalcohol, p-dimethylaminostyrene, N,N-dimethyl-3,5-xylidine, 4-dimethylaminopyridine, N,N-dimethyl-α-naphthylamie N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate and 2,2'-(n-butylimino) diethanol; secondary amines such as N-phenylglycine; barbituric acids such as 5-butylbarbituric acid and 1-benzyl-5-phenylbarbituric acid; tin compounds such as dibutyltin diacetate, dibutyltin dilaurate, dioctyltin dilaurate, dioctyltin diperacetate, dioctyltin bis(mercaptoacetic acid isooctyl ester) salt and tetramethyl-1,3-diacetoxydistannoxane; aldehyde compounds such as laurylaldehyde and terephthalaldehyde; sulfur-containing compounds such as dodecylmercaptan, 2-mercaptobenzooxazole, 1-decanethiol and thiosalicylic acid.

In order to enhance photopolymerization promotion performances, it is effective to add, in addition to the above photopolymerization promoter, oxycarboxylic acids such as citric acid, malic acid, tartaric acid, glycolic acid, gluconic acid, α-oxyisobutyric acid, 2-hydroxypropanoic acid, 3-hydroxypropanoic acid, 3-hydroxybutanoic acid, 4-hydroxybutanoic acid and dimethylolpropionic acid.

These photo polymerization initiators can be used not only singly but also in combinations of two or more. In addition, these photo polymerization initiators have no problem even if subjected to a secondary treatment such as encapsulation in a microcapsule, if necessary.

Furthermore, these photo polymerization initiators can be used not only singly but also in combinations of two or more, regardless of the polymerization manner or the polymerization method.

A content of the photo polymerization initiator (d) may be selected appropriately from a range of 0.01 to 10 parts by weight in external addition based on 100 parts by weight of a total content of a polymerizable monomer component consisting of the acidic group-non-containing polymerizable monomer (a) and the acidic group-containing polymerizable monomer (b), is preferably 0.05 to 7 parts by weight, and is more preferably 0.1 to 5 parts by weight. When the content of the photo polymerization initiator (d) is less than 0.01 parts by weight, a polymerizable monomer is not polymerized and cured sufficiently and therefore it is impossible to obtain high mechanical strength. When the content of the photo polymerization initiator (d) is more than 10 parts by weight, although the polymerization curability to the polymerizable monomer is not changed, a lot of polymerization initiators remain, and there is a risk of causing discoloration.

<Chain Transfer Agent Containing α-alkylstyrene Compound (e)>

The feature of the dental adhesive composition is to contain the chain transfer agent containing α-alkylstyrene compound (e). The effect of the present invention is exhibited only in the case the α-alkylstyrene compound is contained among various chain transfer agents. When other chain transfer agent is only used, although the reduction effect of the polymerization shrinkage stress is recognized, there is a tendency to decrease a polymerization rate, a mechanical characteristic and adhesive property for the tooth substance at the same time, therefore it is impossible that necessary performances for the restoration material are compatible.

Any α-alkyl styrene compounds can be selected depending on a purpose appropriately, without any limitation. Specific examples include 2-phenyl-1-propene, 2,4-diphenyl-4-methyl-1-pentene, 2,4-diphenyl-4-methyl-2-pentene, 3,5-diphenyl-5-methyl-2-heptene, 3,5-diphenyl-5-methyl-3-heptene, 1,3-diphenyl-1-butene, 1,1-diphenyl ethylene. It is preferable that 2,4-diphenyl-4-methyl-1-pentene is used.

Further, other chain transfer agent can be combined to use in addition to the α-alkyl styrene compound to such a range that the effect of the present invention is not prevented, and any know compound may be used without any limitation. Specific examples include mercaptan compounds such as n-butyl mercaptan and n-octyl mercaptan, and terpenoid compounds such as limonene, myrcene, α-terpinene, β-terpinene, γ-terpinene, terpinolene, β-pinene, α-pinene.

A content of the chain transfer agent containing α-alkylstyrene compound (e) may be within a range of 0.01 to 5 parts by weight in external addition based on 100 parts by weight of a the total content of a polymerizable monomer component consisting of the acidic group-non-containing polymerizable monomer (a) and the acidic group-containing polymerizable monomer (b), is preferably 0.05 to 3 parts by weight, and is more preferably 0.1 to 1 parts by weight. When the content of the chain transfer agent containing α-alkylstyrene compound is less than 0.01 parts by weight, there is a risk that an internal distortion caused during the polymerization of the dental adhesive composition is not controlled and therefore sufficient mechanical strength and durable adhesive property are not exhibited. When the content of the chain transfer agent containing α-alkylstyrene compound is more than 5 parts by weight, there is a risk that the chain transfer agent inhibits the polymerization to decrease curing property and there is a risk that a lot of unreacted polymerizable monomers remain in the composition after curing to decrease various kinds of characteristics.

<Other Component>

Besides the components (a) to (e), components such as an excipient represented by fumed silica, an ultraviolet absorber such as 2-hydroxy-4-methylbenzophenone, a polymerization inhibitor such as hydroquinone, hydroquinone monomethyl ether, and 2,5-ditertiarybutyl-4-methylphenol, a discoloration inhibitor, an antibacterial agent, a coloring pigment, and other additives known in the art may be added as necessary and as desired to the dental adhesive composition of the present invention.

Further, water and a solvent miscible with water at a desired ratio may be added as necessary and as desired in consideration of permeability to the tooth substance, decalcification, and biological safety. Examples of the component include alcohols such as methanol, ethanol, and propanol and ketones such as acetone and methylethylketone.

The method of using the dental adhesive composition of the present invention is not specifically limited, and the dental adhesive composition of the present invention may be used not only singly but also in appropriate combination with other treating materials such as an etching agent, a primer, a bonding material, a self-etching primer, a ceramic primer, a metal primer, and a precious metal primer, bonding materials, and filling/restoring materials. Other additives known in the art may be added as necessary and as desired.

In one embodiment of the present invention, the relationship between a refractive index na of a resin component consisting of the acidic group-non-containing polymerizable monomer (a), the acidic group-containing polymerizable monomer (b), the photo polymerization initiator (d) and the chain transfer agent (e) before curing and a refractive index nc of the filler (c) satisfies the following formula (1):

$$|na-nc| \leq 0.01 \tag{1}$$

In this way, it is possible in the dental adhesive composition of the present invention to obtain high transparency from the positional relations of the refractive index between the filler (c) and the resin component, therefore the deep curing depth is exhibited.

In the present specification, 3.5 mm or more of photo curing depth in measuring of the photo curing depth according to ISO 4049, preferably 4.0 mm or more is defined as the deep curing depth.

Although both the photo polymerization initiator and the chain transfer agent are components of the resin and affect the refractive index, because the content is little, it is considered that an influence to the refractive index is few. However, when the contents are large, it is necessary to adjust the mixing ratio and the like including a polymerization initiator as well as a polymerizable monomer because the refractive index is affected.

When a combination of a plurality of fillers is used as the filler (c), because the additivity is established in the refractive index nc of the filler (c), the refractive index nc of the filler (c) can be calculated by adding a refractive index of each filler according to the quantity ratio. However, when the refractive index difference between the fillers to be used is excessively large, even if the above formula (1) is satisfied, there is a possibility that the composition becomes opaque by generating cloudiness and curing depth decreases. Therefore, when a combination of a plurality of fillers is used, the above formula (1) is satisfied by preferably at least 40% by weight, more preferably 50 or more % by weight, further preferably 60 or more % by weight of the filler in the 100% by weight of the filler (c).

It is also preferable to treat the surface of the filler (c) by a surface treatment method using a surface treatment agent or the like in order to increase the functionality of the filler. Such surface-treated filler may also be used without any limitation for the dental adhesive composition of the present invention. In this case, it is only necessary that the refractive index nc of the filler (c) before the surface treatment method is applied to increase the functionality of the filler should meet the relationship (1).

While a variety of color expression systems are used in the dental field as a method of measuring and quantifying the color tone of dental materials such as the tooth substance, artificial teeth, porcelain, and hard resins, a contrast ratio defined using a Y value for brightness among three stimulating values or tristimulus values in an XYZ color expression system prescribed according to JIS Z8701 is used as a method of quantifying the opacity of a dental filling material.

The contrast ratio is obtained by placing a disk-shaped test specimen of a certain thickness on a standard white background and a standard black background, illuminating the test specimen and the background under certain conditions (such as light source and irradiated area), measuring the brightness (Yw) of the white background and the brightness (Yb) of the black background, and calculating the contrast ratio using a specific formula. The contrast ratio is affected by the thickness of the test specimen. Thus, the contrast ratio is calculated using the formula (2) provided in "Dental Materials and Appliances Vol. 14, Special Issue 26" (1995), which includes a correction for the thickness of the specimen to obtain a more accurate contrast ratio.

$$\text{Contrast ratio}=1-(1-Yw/Yb)^{(1/L)} \tag{2}$$

The material is more opaque as the value of the contrast ratio is closer to 1, and more transparent as the value of the contrast ratio is closer to 0.

In the dental adhesive composition of the present invention, when the relationship between a refractive index na of a resin component consisting of the acidic group-non-containing polymerizable monomer (a), the acidic group-containing polymerizable monomer (b), the photo polymerization initiator (d) and the chain transfer agent (e) before curing and a refractive index nc of the filler (c) satisfies the above formula (1), the value of the contrast ratio before curing is 0.5 or less, preferably 0.4 or less.

When the contrast ratio of the dental adhesive composition of the present invention before curing is more than 0.5, the transparency of the dental adhesive composition may be too low, therefore there is a risk of decreasing the photo curing depth. In addition, there is a risk of decreasing the polymerization rate of the dental adhesive composition of the present invention to decrease adhesive property.

Furthermore, in the dental adhesive composition of the present invention, when the relationship between a refractive index na of a resin component consisting of the acidic group-non-containing polymerizable monomer (a), the acidic group-containing polymerizable monomer (b), the photo polymerization initiator (d) and the chain transfer agent (e) before curing and a refractive index nc of the filler (c) satisfies the above formula (1), the refractive index of the resin increase after curing, therefore the refractive index difference between the refractive index nc of the filler (c) becomes large. As a result, the composition becomes opaque after curing, and the value of the contrast ratio after curing becomes within a range of 0.4 to 0.8, and appropriate opaque can shield the color of a background such as a cavity wall to obtain superior aesthetic property without being affected by the background color.

EXAMPLES

Hereinafter, Example of the present invention are specifically described. However, the present invention is not intended to be limited to these Examples.

The test methods adopted in Examples and Comparative examples are as follows.
(1) Measurement of Refractive Index of Filler Several types of immersion liquids for refractive index measurement having a desired refractive index were prepared in advance using tricresyl phosphate and dioctyl adipate (both manufactured by Daihachi Chemical Industry Co., Ltd.). After a small amount of the filler was placed on a slide glass in a thermostatic chamber at 25° C., several drops of the prepared immersion liquids were dropped. After the mixture was mixed to be uniform, a cover glass was placed to obtain a measurement sample. When the measurement sample became most transparent, the refractive index of the immersion liquid was measured as the refractive index of the filler.

(2) Measurement of Refractive Index of Poylmerizable Monomer

The refractive index (at 25° C.) of the prepared resin component was measured using an Abbe refractometer (2T type manufactured by Atago Co., Ltd.).

(3) Measurement of Opacity

Each prepared dental adhesive composition was fully injected into a mold (in a shape of a disc having a diameter of 15 mm and a thickness of 1 mm) made of stainless steel. Then, a cover glass was placed on the mold from above, and pressed against the mold using a glass plate. While leaving the cover glass intact, each specimen was placed on the background of a standard white background (D65/10° X=81.07, Y=86.15, Z=93.38) and a standard black background (D65/10° X=0.0, Y=0.0, Z=0.0), and illuminated under predetermined constant conditions (light source: C, viewing angle: 2°, measurement area: 11 mm) using a color-guide spectrocolorimeter (manufactured by BYK-Chemie GmbH) to measure the brightness (Yw) of the white background and the brightness (Yb) of the black background before curing.

After that, the dental composition was irradiated with light from above the cover glass for 1 minute using a photo polymerization irradiator (Grip Light II manufactured by Shofu Inc.) to be cured. Thereafter, the cured object was taken out of the mold to obtain a test specimen and the brightness (Yw) of the white background and the brightness (Yb) of the black background of the test specimen was measured according to the above described procedure. After that, the thickness of the test specimen was measured at 5 points using a micrometer, and the average of the thicknesses was determined as the thickness of the test specimen. The contrast ratio (C) of the dental adhesive composition before curing and after curing was calculated from the formula (2) based on Yw and Yb before curing and after curing and the measured value of the thicknesses of the test specimen.

(4) Tooth Substance Adhesion Test

A narrow piece of a cow tooth was prepared by extracting a permanent mandibular central incisor, freezing the incisor within 24 hours and unfreezing the incisor, and removing the root portion and cutting away the crown portion. The narrow piece of the cow tooth was embedded in an epoxy resin. The embedded cow tooth was sanded using #600 waterproof abrasive paper to expose an enamel or a dentin, and then washed with water and dried.

A double-sided tape with a hole having a diameter of 4 mm was affixed to the exposed enamel or dentin to prescribe an adhesion surface. A plastic mold (inside diameter: 4 mm, height: 2 mm or 4 mm) was fixed to the prescribed surface, and the dental adhesive composition was injected onto the adhesion surface, and irradiated with light for 20 seconds using a photo polymerization irradiator (Grip Light II manufactured by Shofu Inc.) to be cured. After that, the mold was removed to prepare an adhesion test specimen. The adhesion test specimen was immersed in distilled water at 37° C. for 24 hours. After that, a tooth substance adhesion test was performed for shear bond strength, using an Instron universal testing machine (Instron 5567 manufactured by Instron) at a crosshead speed of 1 mm/min to measure an initial adhesive strength.

Further, after immersion in 37° C. for 24 hours and then 2000 times of thermal cycle, a tooth substance adhesion test was performed for the prepared test specimen to measure a durable adhesive strength.

(5) Bending Strength

The prepared dental adhesive composition was filled into a stainless steel mold, and the cover glasses were placed on both sides to press with a glass kneading plate. Thereafter, light is irradiated for 10 seconds to 5 locations by using the photopolymerization irradiator (Blue Shot manufactured SHOFU Inc.) to curing the dental adhesive composition. After curing, the cured product was removed from the mold, and light is irradiated to the backside in the same manner again to use as a test specimen (25×2×2 mm rectangular shape). The test specimen was immersed in water at 37° C. for 24 hours, and thereafter bending test was performed.

Bending test was performed using an Instron universal tester (Instron 5567 manufactured by Instron) at a distance between supporting points of 20 mm and a crosshead speed of 1 mm/min.

The number of the test specimen is 10 and the bending strength is evaluated by the average.

(6) Polymerization Shrinkage Stress

A primer for metal was applied on an iron plate (material: SPCC, inside diameter: 10 mm, thickness 1 mm) stuck with a strain gauge (KFG-2-120-C1-11 manufactured by Kyowa Electronic Instruments Co., Ltd.), and thereafter it was placed into a ring-formed die (inside diameter: 10 mm, thickness 2 mm) made by fluoric resin. The dental adhesive composition is filled on a primer application surface with a thickness of 1 mm. The light was irradiated from above and the strain of the iron plate due to the curing was measured. Polymerization shrinkage stress was calculated by multiplying the value of the strain after 600 seconds or after 24 hours from the light irradiation, and the elastic modulus of the iron plate based on the formula (3).

$$\text{Polymerization shrinkage stress (MPa)}=\varepsilon \times E \quad (3)$$

ε: Strain
E: Elastic modulus (7) Polymerization Rate

The infrared absorption spectrum of the prepared dental adhesive composition was measured with the KBR method of the infrared absorption spectrometer (JASCO FT-IR-6300, manufactured by JASCO Corp.) (measuring range: 400 to 4000 cm$^1$). The peak heights (h) belonging to a (meth)acrylate double bond (1637 cm$^{-1}$) and a carbonyl group (1717 cm$^{-1}$) of the dental adhesive composition before curing was measured. The amount of non-polymerization monomer of each material was obtained by the ratio (Ib) of the peak height before curing of double bond (1637 cm$^{-1}$)/carbonyl group (1717 cm$^{-1}$). Thereafter, light is irradiated for 10 seconds by using the photopolymerization irradiator (Blue Shot manufactured SHOFU Inc.) to curing the dental adhesive composition. The peak heights (h) belonging to a (meth)acrylate double bond (1637 cm$^{-1}$) and a carbonyl group (1717 cm$^{-1}$) of the dental adhesive composition were measured immediately after light irradiation and after 24 hours according to the above procedure and the ratio (Ia) of the peak height after curing was obtained. Polymerization rates (%) immediately after light irradiation and after 24 hours were calculated from the formula (4) based on the obtained peak heights before curing and after curing.

$$\text{Polymerization rate (\%)}=100-Ia/Ib \times 100 \quad (4)$$

(8) Photo Curing Depth

The prepared dental adhesive composition was filled into a stainless steel mold having a diameter of 4 mm and a thickness of 12 mm, and the cover glasses were placed on both sides to press with a glass kneading plate. Thereafter, light is irradiated for 10 seconds by using the photopolymerization irradiator (Blue Shot manufactured SHOFU Inc.) to cure the dental adhesive composition. After curing, the cured product was removed from the mold, non-polymerized paste was removed with a spatula made by plastic. Thereafter, the thickness of the cured product was measured by a micrometer and the value of ½ of the measured value was defined photo curing depth (mm).

The materials used in Examples and Comparative examples and their abbreviations are listed below.

[Acidic Group-Non-Containing Polymerizable Monomer (a)]
Bis-GMA: 2,2-bis(4-(3-methacryloyloxy-2-hydroxypropoxy)phenyl)propane (refractive index before curing: 1.552)
UDMA: N,N-(2,2,4-trimethyl hexamethylene) bis [2-(aminocarboxy) ethanol] methacrylate (refractive index before curing: 1.483)
3G: triethylene glycol dimethacrylate (refractive index before curing: 1.460)

[Acid Group-Containing Polymerizable Monomer (b)]
6-MHPA: (6-methacryloxy) hexylphosphonoacetate (refractive index before curing: 1.473)
10-MDP: 10-methacryloxy decyl dihydrogen phosphate (refractive index before curing: 1.468)

[Acidic Group-Non-Containing Hydrophilic Polymerizable Monomer (f)]
HEMA: 2-hydroxyethylmethacrylate (refractive index before curing: 1.451)
701A: 2-hydroxy-3-acryloiloxy propylmethacrylate (refractive index before curing: 1.471)

[Filler (c)]
Refractive indexes and average particle diameters of Inorganic particles 1 to 3 of the filler used for preparing the dental adhesive compositions were measured. The results are shown in Table 1. These inorganic particles were each appropriately subjected to a silane treatment and used for preparation of the dental adhesive compositions.

TABLE 1

|  | Refractive index | Average particle diameter (μm) |
|---|---|---|
| Inorganic particle-1 | 1.480 | 2.96 |
| Inorganic particle-2 | 1.510 | 0.46 |
| Inorganic particle-3 | 1.522 | 1.51 |

[Polymerization Initiator (d)]
CQ: camphorquinone
DMABE: ethyl N,N-dimethylaminobenzoate

[Chain Transfer Agent (e)]
α-MSD: 2,4-diphenyl-4-methyl-1-pentene
DMH: 3,5-diphenyl-5-methyl-2-heptene
γ-terpinene
TEMPO: 2,2,6,6,-tetramethylpiperidine 1-oxyl free radical

[Preparation of Resin Components (I1 to I21)]
Resin components (I1 to I21) were prepared according to the compositions shown in Table 2.

TABLE 2

| | Content (part by weight) | | | | | | | | | | | | |
|---|---|---|---|---|---|---|---|---|---|---|---|---|---|
| | Acidic group-non-containing polymerizable monomer (a) | | | Acidic group-non-containing hydrophilic polymerizable monomer (f) | | Acidic group-containing polymerizable monomer (b) | | Photo polymerization initiator (d) | | Chain transfer agent (e) | | | | Refractive index of resin component before curing |
| | UDMA | Bis-GMA | 3G | HEMA | 701A | 10-MDP | 6-MHPA | CQ | DMBE | α-MSD | DMH | γ-terpinene | TEMPO | (na) |
| I1 | 54 | | | 36 | | | 10 | 0.3 | 0.3 | 0.3 | | | | 1.47 |
| I2 | 54 | | | 36 | | | 10 | 0.3 | 0.3 | 0.7 | | | | 1.47 |
| I3 | 54 | | | 36 | | | 10 | 0.3 | 0.3 | 5 | | | | 1.47 |
| I4 | 54 | | 36 | | | | 10 | 0.3 | 0.3 | 0.3 | | | | 1.474 |
| I5 | 59 | | | | 40 | | 1 | 0.3 | 0.3 | 0.5 | | | | 1.471 |
| I6 | | 35 | | 35 | | 15 | 15 | 0.3 | 0.3 | 0.7 | | | | 1.492 |
| I7 | | 27 | | | 63 | | 10 | 0.3 | 0.3 | 0.7 | | | | 1.493 |
| I8 | 70 | | | 17 | | 3 | 10 | 0.3 | 0.3 | 0.1 | | | | 1.476 |
| I9 | 54 | | 31 | 5 | | | 10 | 0.3 | 0.3 | 0.7 | | | | 1.473 |
| I10 | | 52 | | | 35 | 13 | | 0.3 | 0.3 | 1 | | | | 1.513 |
| I11 | 54 | | | 36 | | | 10 | 0.3 | 0.3 | | 0.3 | | | 1.47 |
| I12 | 54 | | | 36 | | | 10 | 0.3 | 0.3 | | 0.7 | | | 1.47 |
| I13 | 54 | | 36 | | | | 10 | 0.3 | 0.3 | | | | | 1.474 |
| I14 | 54 | | | 36 | | | | 0.3 | 0.3 | 0.3 | | | | 1.47 |
| I15 | 54 | | | 36 | | | 10 | 0.3 | 0.3 | | | 0.3 | | 1.47 |
| I16 | 54 | | | 36 | | | 10 | 0.3 | 0.3 | | | 0.7 | | 1.47 |
| I17 | 54 | | | 36 | | | 10 | 0.3 | 0.3 | | | | 0.3 | 1.47 |
| I18 | 54 | | | 36 | | | 10 | 0.3 | 0.3 | | | | 0.7 | 1.47 |
| I19 | 54 | | | 36 | | | 10 | 0.3 | 0.3 | 0.01 | | | | 1.47 |
| I20 | 54 | | | 36 | | | 10 | 0.05 | 0.05 | 0.3 | | | | 1.47 |
| I21 | 54 | | | 36 | | | 10 | 5 | 5 | 0.3 | | | | 1.47 |

[Preparation of Dental Self-Adhesive Restoration Material]

The dental self-adhesive restoration materials (Examples 1 to 17 and Comparative example 1 to 6) were prepared by using the resin components described in Table 2 according to the composition described in Table 3.

TABLE 3

| | Type of resin component (1) | Amount of resin component (1) | (c) Filler | | |
|---|---|---|---|---|---|
| | | | Inorganic filler 1 | Inorganic filler 2 | Inorganic filler 3 |
| Refractive Index | | | 1.48 | 1.51 | 1.522 |
| Example 1 | I1 | 30 | 70 | | |
| Example 2 | I2 | 30 | 70 | | |
| Example 3 | I3 | 30 | 70 | | |
| Example 4 | I4 | 30 | 70 | | |
| Example 5 | I5 | 60 | 40 | | |
| Example 6 | I6 | 10 | | | 90 |
| Example 7 | I7 | 50 | 50 | | |
| Example 8 | I8 | 40 | 60 | | |
| Example 9 | I9 | 30 | 70 | | |
| Example 10 | I10 | 50 | | 50 | |
| Example 11 | I11 | 30 | 70 | | |
| Example 12 | I12 | 30 | 70 | | |
| Example 13 | I1 | 30 | | | 70 |
| Example 14 | I10 | 50 | | 25 | 25 |
| Comparative example 1 | I13 | 30 | 70 | | |
| Comparative example 2 | I14 | 30 | 70 | | |
| Comparative example 3 | I15 | 30 | 70 | | |
| Comparative example 4 | I16 | 30 | 70 | | |
| Comparative example 5 | I17 | 30 | 70 | | |
| Comparative example 6 | I18 | 30 | 70 | | |
| Example 15 | I19 | 30 | 70 | | |
| Example 16 | I20 | 30 | 70 | | |
| Example 17 | I21 | 30 | 70 | | |

The suitability for the formula (1) was evaluated by the relationship of the refractive indexes of the filler and the resin component contained in the dental self-adhesive restoration material (Examples 1 to 17 and Comparative examples 1 to 6). The results are shown in Table 4.

$$|na-nc| \leq 0.01 \quad (1)$$

TABLE 4

| | Refractive index | | | Suitability for formula (1) | Contrast ratio | |
|---|---|---|---|---|---|---|
| | Resin component na | Filler nc | $|na - nc|$ | | Before curing | After curing |
| Example 1 | 1.47 | 1.48 | 0.01 | ○ | 0.32 | 0.46 |
| Example 2 | 1.47 | 1.48 | 0.01 | ○ | 0.32 | 0.47 |
| Example 3 | 1.47 | 1.48 | 0.01 | ○ | 0.33 | 0.47 |
| Example 4 | 1.474 | 1.48 | 0.006 | ○ | 0.25 | 0.48 |
| Example 5 | 1.471 | 1.48 | 0.009 | ○ | 0.28 | 0.45 |
| Example 6 | 1.492 | 1.522 | 0.03 | x | 0.47 | 0.25 |
| Example 7 | 1.493 | 1.48 | 0.013 | x | 0.37 | 0.57 |
| Example 8 | 1.476 | 1.48 | 0.004 | ○ | 0.22 | 0.48 |
| Example 9 | 1.473 | 1.48 | 0.007 | ○ | 0.26 | 0.51 |
| Example 10 | 1.513 | 1.51 | 0.003 | ○ | 0.2 | 0.5 |
| Example 11 | 1.47 | 1.48 | 0.01 | ○ | 0.32 | 0.46 |
| Example 12 | 1.47 | 1.48 | 0.01 | ○ | 0.33 | 0.47 |
| Example 13 | 1.47 | 1.522 | 0.052 | x | 0.61 | 0.44 |
| Example 14 | 1.513 | 1.516 | 0.003 | ○ | 0.23 | 0.46 |
| Comparative example 1 | 1.474 | 1.48 | 0.006 | ○ | 0.25 | 0.47 |
| Comparative example 2 | 1.47 | 1.48 | 0.01 | ○ | 0.33 | 0.43 |
| Comparative example 3 | 1.47 | 1.48 | 0.01 | ○ | 0.33 | 0.43 |
| Comparative example 4 | 1.47 | 1.48 | 0.01 | ○ | 0.33 | 0.43 |
| Comparative example 5 | 1.47 | 1.48 | 0.01 | ○ | 0.33 | 0.43 |
| Comparative example 6 | 1.47 | 1.48 | 0.01 | ○ | 0.33 | 0.43 |
| Example 15 | 1.47 | 1.48 | 0.01 | ○ | 0.32 | 0.46 |
| Example 16 | 1.47 | 1.48 | 0.01 | ○ | 0.32 | 0.46 |
| Example 17 | 1.47 | 1.48 | 0.01 | ○ | 0.34 | 0.49 |

The evaluation results in the dental self-adhesive restoration material of the Examples 1 to 17 and the Comparative example 1 to 6 are shown in Table 5 and Table 6.

TABLE 5

| | Polymerization rate (%) | | Polymerization shrinkage stress (Mpa) | | Bending strength (Mpa) | Photo curing depth (mm) |
|---|---|---|---|---|---|---|
| | Immediately after | after 24 hours | after 600 seconds | after 24 hours | | |
| Example 1 | 38 | 81 | 2.9 | 3.9 | 134 | 4.6 |
| Example 2 | 36 | 82 | 1.2 | 2.3 | 130 | 4.4 |
| Example 3 | 25 | 73 | 0 | 0.5 | 116 | 4.1 |
| Example 4 | 37 | 83 | 2.2 | 3.1 | 140 | 5.1 |
| Example 5 | 39 | 82 | 2.7 | 3.4 | 129 | 4.7 |
| Example 6 | 36 | 78 | 4.2 | 5.8 | 131 | 2.8 |
| Example 7 | 35 | 81 | 2.4 | 5.3 | 122 | 3.4 |
| Example 8 | 47 | 83 | 5.8 | 7.1 | 136 | 5.2 |
| Example 9 | 38 | 80 | 3.3 | 3.8 | 140 | 4.9 |
| Example 10 | 30 | 77 | 1.7 | 2.7 | 132 | 5 |
| Example 11 | 48 | 80 | 6 | 7.7 | 136 | 4.8 |
| Example 12 | 44 | 82 | 5.5 | 7.2 | 131 | 4.6 |
| Example 13 | 36 | 82 | 2.7 | 4 | 135 | 2.8 |
| Example 14 | 31 | 84 | 2 | 3.5 | 129 | 4.7 |

TABLE 5-continued

|  | Polymerization rate (%) | | Polymerization shrinkage stress (Mpa) | | Bending strength (Mpa) | Photo curing depth (mm) |
|---|---|---|---|---|---|---|
|  | Immediately after | after 24 hours | after 600 seconds | after 24 hours | | |
| Comparative example 1 | 61 | 80 | 9.2 | 13.7 | 145 | 4.9 |
| Comparative example 2 | 41 | 84 | 2 | 4.4 | 134 | 4.4 |
| Comparative example 3 | 53 | 82 | 4.5 | 12.5 | 112 | 4.4 |
| Comparative example 4 | 50 | 83 | 2.7 | 11.3 | 97 | 4.1 |
| Comparative example 5 | 62 | 84 | 9 | 13.5 | 131 | 3.8 |
| Comparative example 6 | 63 | 84 | 8.2 | 13.2 | 129 | 3.1 |
| Example 15 | 52 | 85 | 6.7 | 7.9 | 138 | 4.8 |
| Example 16 | 27 | 52 | 0.8 | 1.3 | 103 | 4 |
| Example 17 | 40 | 83 | 3.2 | 4.1 | 142 | 4.8 |

TABLE 6

|  | Adhesive strength too dentin (Mpa) | | | | Adhesive strength too enamel (Mpa) | | | |
|---|---|---|---|---|---|---|---|---|
|  | 2 mm thcikness | | 4 mm thcikness | | 2 mm thcikness | | 4 mm thcikness | |
|  | Initial | Durable | Initial | Durable | Initial | Durable | Initial | Durable |
| Example 1 | 12.6 | 14 | 11.2 | 12.5 | 13.9 | 12.2 | 12.1 | 11.6 |
| Example 2 | 12.8 | 13.5 | 12.6 | 13.2 | 14.2 | 12.7 | 13.7 | 12.4 |
| Example 3 | 12.9 | 14.5 | 12.8 | 14.2 | 14.4 | 13.5 | 14.2 | 13.5 |
| Example 4 | 8.1 | 7.4 | 8.3 | 7.1 | 11 | 9.2 | 11.2 | 10.1 |
| Example 5 | 7.2 | 7 | 7.3 | 7 | 7.6 | 6.8 | 7.3 | 6.7 |
| Example 6 | 8.9 | 9.3 | 7.6 | 7.2 | 8.5 | 8 | 7.4 | 7 |
| Example 7 | 12.6 | 13.5 | 10.2 | 11.5 | 12.4 | 13.6 | 10.5 | 9.2 |
| Example 8 | 9.5 | 9 | 9 | 8.3 | 11.8 | 10 | 10.5 | 10.1 |
| Example 9 | 9.3 | 10.3 | 10.1 | 10.8 | 11.9 | 10.5 | 11.3 | 10.4 |
| Example 10 | 13.3 | 14.5 | 13.5 | 14 | 14.4 | 14.1 | 13.9 | 13.4 |
| Example 11 | 7.9 | 8.4 | 7.5 | 8.2 | 10.2 | 9.3 | 9.7 | 9 |
| Example 12 | 8.1 | 8.5 | 7.6 | 8.9 | 11 | 10.2 | 10.3 | 9.5 |
| Example 13 | 12.2 | 14.2 | 8.3 | 7.7 | 13.8 | 12.5 | 9.7 | 8.3 |
| Example 14 | 13.1 | 13.8 | 12.7 | 13.5 | 14.5 | 13.3 | 13.2 | 12.5 |
| Comparative example 1 | 7.3 | Some falling off | 6.1 | Some falling off | 8.8 | Some falling off | 7.4 | Some falling off |
| Comparative example 2 | All falling off | — | All falling off | — | All falling off | — | All falling off | — |
| Comparative example 3 | 8.1 | 3.2 | 6.3 | Some falling off | 8.9 | 3.5 | 7.3 | Some falling off |
| Comparative example 4 | 8.3 | 2.8 | 4.8 | All falling off | 9.2 | 3.3 | 7.1 | All falling off |
| Comparative example 5 | 5.8 | Some falling off | 3.1 | All falling off | 7.5 | Some falling off | 3.8 | All falling off |
| Comparative example 6 | 6 | Some falling off | All falling off | — | 6.1 | Some falling off | All falling off | — |
| Example 15 | 7.1 | 4.2 | 6.8 | 3.4 | 9.5 | 4.8 | 8 | 4.3 |
| Example 16 | 5.3 | 2.8 | 4.7 | 2 | 6.3 | 3.4 | 5.8 | 2.7 |
| Example 17 | 12.5 | 12.7 | 10.9 | 11.3 | 13.2 | 12.5 | 12 | 10.7 |

Examples 1 to 17

In the dental self-adhesive restoration materials of the Examples 1 to 17, it was recognized that although the polymerization rate was low immediately after light irradiation, the polymerization rate increased after 24 hours. In addition, the polymerization shrinkage stress was low in both after 600 seconds and after 24 hours, and therefore the bending strength was high. In other words, it was understood that it was possible to delay the gelation point in initial polymerization effectively without preventing the final polymerization rate by containing α-alkylstyrene compound as the chain transfer agent and as a result, both low polymerization shrinkage stress and good bending strength were compatible. Furthermore, it was recognized that the durable adhesive strength was high value in both a dentin and an enamel, and it had stable self-adhesive property to a tooth substance.

Furthermore, in the dental self-adhesive restoration material of Examples 1 to 5, 8 to 12 and 14 to 17 which satisfied the formula (1) and had high transparency before curing, it was recognized that since the photo curing depth is 4 mm or more, adhesive strength to a dentin and an enamel did not decrease in the case of 4 mm thickness.

Comparative Example 1

Since the dental self-adhesive restoration material of the Comparative example 1 did not a chain transfer agent, it was recognized that the polymerization rate was high and the polymerization shrinkage stress was high immediately after light irradiation. In addition, with respect to adhesive strength to a dentin and an enamel, although this dental self-adhesive restoration material had adhesive property in initial, the falling off of the test specimen occurred in the durable adhesive test, therefore it was recognized that adhesive property decreased.

Comparative Example 2

The dental self-adhesive restoration material of the Comparative example 2 contained an α-alkylstyrene compound as the chain transfer agent, however, did not contain an acid group-containing polymerizable monomer. Therefore, this dental self-adhesive restoration material exhibited low polymerization shrinkage stress, however did not have adhesive property to the tooth substance.

Comparative Examples 3 to 6

In Comparative examples 3 to 6, the dental self-adhesive restoration materials contained the chain transfer agent other than α-alkylstyrene compound, therefore the suppressive effect of the polymerization rate immediately after the light irradiation was low. In Comparative examples 3 and 4 in which γ-terpinene was used, although the polymerization shrinkage stress was reduced after 600 seconds from the light irradiation, the polymerization shrinkage stress increased after 24 hours, and it was recognized that there was a tendency that the bending strength decreased. In addition, the dental self-adhesive restoration materials of Comparative examples 3 to 6, it was recognized that adhesive strength to a dentin and an enamel was remarkably low and the falling off of the test specimen occurred frequently in the durable adhesive test.

While a one-paste type dental self-adhesive restoration material has been described above, it is a matter of course that the present invention may also be applied to dental adhesive compositions obtained by mixing two or more pastes or liquids.

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

INDUSTRIAL APPLICABILITY

The present invention provides a one paste type dental adhesive composition which has mechanical characteristics and aesthetic property required in the restoration material, is superior in durable adhesive strength to the tooth substance, and is hard to be affected by the polymerization shrinkage stress and exhibits excellent durable adhesive strength even if the composition of the present invention is collectively filled and cured.

What is claimed is:

1. A one paste dental adhesive composition comprising:
    (a) an acidic group-non-containing polymerizable monomer,
    (b) an acidic group-containing polymerizable monomer,
    (c) a filler,
    (d) a photo polymerization initiator, and
    (e) a chain transfer agent, wherein
    the chain transfer agent (e) contains an α-alkylstyrene compound.

2. The one paste dental adhesive composition according to claim 1, wherein
    the one paste dental adhesive composition comprises the acidic group-non-containing polymerizable monomer (a) and the acid group-containing polymerizable monomer (b) in a weight ratio of the acidic group-non-containing polymerizable monomer (a): the acid group-containing polymerizable monomer (b)=99:1 to 70:30.

3. The one paste dental adhesive composition according to claim 2, wherein
    the one paste dental adhesive composition comprises
    0.01 to 10 parts by weight of the photo polymerization initiator (d) and 0.01 to 5 parts by weight of the chain transfer agent (e) based on 100 parts by weight of a total content of a polymerizable monomer component consisting of the acidic group-non-containing polymerizable monomer (a) and the acidic group-containing polymerizable monomer (b), and
    50 to 900 parts by weight of the filler (c) based on 100 parts by weight a total content of a resin component consisting of the acidic group-non-containing polymerizable monomer (a), the acidic group-containing polymerizable monomer (b), the photo polymerization initiator (d) and the chain transfer agent (e).

4. The one paste dental adhesive composition according to claim 1, wherein
    the one paste dental adhesive composition comprises 5 to 70 parts by weight of (f) an acidic group-non-containing hydrophilic polymerizable monomer in 100 parts by weight of the acidic group-non-containing polymerizable monomer (a).

5. The one paste dental adhesive composition according to claim 1, wherein
    the chain transfer agent (e) is 2,4-diphenyl-4-methyl-1-pentene.

6. The one paste dental adhesive composition according to claim 1, wherein
    a relationship between a refractive index na of a resin component consisting of the acidic group-non-containing polymerizable monomer (a), the acidic group-containing polymerizable monomer (b), the photo polymerization initiator (d) and the chain transfer agent (e) before curing and a refractive index nc of the filler (c) satisfies the following formula (1):

$$|na-nc| \leq 0.01 \tag{1}.$$

7. The one paste dental adhesive composition according to claim 2, wherein
    the one paste dental adhesive composition comprises 5 to 70 parts by weight of (f) an acidic group-non-containing hydrophilic polymerizable monomer in 100 parts by weight of the acidic group-non-containing polymerizable monomer (a).

8. The one paste dental adhesive composition according to claim 3, wherein
    the one paste dental adhesive composition comprises 5 to 70 parts by weight of (f) an acidic group-non-containing hydrophilic polymerizable monomer in 100 parts by weight of the acidic group-non-containing polymerizable monomer (a).

9. The one paste dental adhesive composition according to claim 2, wherein
the chain transfer agent (e) is 2,4-diphenyl-4-methyl-1-pentene.

10. The one paste dental adhesive composition according to claim 3, wherein
the chain transfer agent (e) is 2,4-diphenyl-4-methyl-1-pentene.

11. The one paste dental adhesive composition according to claim 4, wherein
the chain transfer agent (e) is 2,4-diphenyl-4-methyl-1-pentene.

12. The one paste dental adhesive composition according to claim 2, wherein
a relationship between a refractive index na of a resin component consisting of the acidic group-non-containing polymerizable monomer (a), the acidic group-containing polymerizable monomer (b), the photo polymerization initiator (d) and the chain transfer agent (e) before curing and a refractive index nc of the filler (c) satisfies the following formula (1):

$$|na-nc| \leq 0.01 \tag{1}.$$

13. The one paste dental adhesive composition according to claim 3, wherein
a relationship between a refractive index na of the resin component consisting of the acidic group-non-containing polymerizable monomer (a), the acidic group-containing polymerizable monomer (b), the photo polymerization initiator (d) and the chain transfer agent (e) before curing and a refractive index nc of the filler (c) satisfies the following formula (1):

$$|na-nc| \leq 0.01 \tag{1}.$$

14. The one paste dental adhesive composition according to claim 4, wherein
a relationship between a refractive index na of a resin component consisting of the acidic group-non-containing polymerizable monomer (a), the acidic group-containing polymerizable monomer (b), the photo polymerization initiator (d) and the chain transfer agent (e) before curing and a refractive index nc of the filler (c) satisfies the following formula (1):

$$|na-nc| \leq 0.01 \tag{1}.$$

15. The one paste dental adhesive composition according to claim 5, wherein
a relationship between a refractive index na of a resin component consisting of the acidic group-non-containing polymerizable monomer (a), the acidic group-containing polymerizable monomer (b), the photo polymerization initiator (d) and the chain transfer agent (e) before curing and a refractive index nc of the filler (c) satisfies the following formula (1):

$$|na-nc| \leq 0.01 \tag{1}.$$

16. A dental adhesive composition comprising:
(a) an acidic group-non-containing polymerizable monomer,
(b) an acidic group-containing polymerizable monomer,
(c) a filler,
(d) a photo polymerization initiator,
(e) a chain transfer agent, and
(f) an acidic group-non-containing hydrophilic polymerizable monomer, wherein
the chain transfer agent (e) contains an α-alkylstyrene compound, and
the dental adhesive composition comprises 5 to 70 parts by weight of the (f) an acidic group-non-containing hydrophilic polymerizable monomer in 100 parts by weight of the acidic group-non-containing polymerizable monomer (a).

17. The dental adhesive composition according to claim 16, wherein
the dental adhesive composition comprises the acidic group-non-containing polymerizable monomer (a) and the acid group-containing polymerizable monomer (b) in a weight ratio of the acidic group-non-containing polymerizable monomer (a): the acid group-containing polymerizable monomer (b)=99:1 to 70:30.

18. The dental adhesive composition according to claim 16, wherein
the dental adhesive composition comprises
0.01 to 10 parts by weight of the photo polymerization initiator (d) and 0.01 to 5 parts by weight of the chain transfer agent (e) based on 100 parts by weight of a total content of a polymerizable monomer component consisting of the acidic group-non-containing polymerizable monomer (a) and the acidic group-containing polymerizable monomer (b), and
50 to 900 parts by weight of the filler (c) based on 100 parts by weight a total content of a resin component consisting of the acidic group-non-containing polymerizable monomer (a), the acidic group-containing polymerizable monomer (b), the photo polymerization initiator (d) and the chain transfer agent (e).

19. The dental adhesive composition according to claim 16, wherein
the chain transfer agent (e) is 2,4-diphenyl-4-methyl-1-pentene.

20. The dental adhesive composition according to claim 16, wherein
a relationship between a refractive index na of a resin component consisting of the acidic group-non-containing polymerizable monomer (a), the acidic group-containing polymerizable monomer (b), the photo polymerization initiator (d) and the chain transfer agent (e) before curing and a refractive index nc of the filler (c) satisfies the following formula (1):

$$|na-nc| \leq 0.01 \tag{1}.$$

* * * * *